United States Patent
Katsumoto et al.

(10) Patent No.: US 8,478,546 B2
(45) Date of Patent: Jul. 2, 2013

(54) METHOD FOR MEASURING PHYSICAL PROPERTY VALUES OF A CELL

(75) Inventors: Yoichi Katsumoto, Tokyo (JP); Yoshihito Hayashi, Chiba (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 12/733,031

(22) PCT Filed: Jul. 28, 2008

(86) PCT No.: PCT/JP2008/063500
§ 371 (c)(1),
(2), (4) Date: Feb. 3, 2010

(87) PCT Pub. No.: WO2009/022536
PCT Pub. Date: Feb. 19, 2009

(65) Prior Publication Data
US 2010/0136606 A1    Jun. 3, 2010

(30) Foreign Application Priority Data
Aug. 10, 2007  (JP) .................................. 2007-209108

(51) Int. Cl.
*G01N 33/48*    (2006.01)
(52) U.S. Cl.
USPC ......................................................... 702/21
(58) Field of Classification Search
None
See application file for complete search history.

(56) References Cited

U.S. PATENT DOCUMENTS
2012/0137753 A1    6/2012    Hayashi

FOREIGN PATENT DOCUMENTS
JP    2003-507739    2/2003
JP    2005-512042    4/2005

OTHER PUBLICATIONS

Kaatze (J. Chem. Eng. Data, 1989, 34, 371-374).*
Asami et al. (J. Phys. D: Appl. Phys., 2006, 39: 492-499).*
Katsuhisa Sekine et al., "Calculation of dielectric spectra of suspensions of rod-shaped cells using boundary element method", Bioelectrochemistry, 2002, vol. 57, pp. 83-87.
Koji Asami, "Characterization of heterogeneous systems of dielectric spectroscopy", Prg. Polym. Sci., 2002, vol. 27, pp. 1617-1659.
Katsuhisa Sekine et al., "Boundary-element calculations for dielectric behavior of doublet-shaped cells", Biochimica et Biophysica Acta, 2005, vol. 1721, pp. 130-138.
Asami, Dielectric moderation simulation of the various types of cell. Collection of Membrane Society of Japan, No. 27. Lecture subject matter. Apr. 30, 2005, p. 62.
Asami, Dielectric spectrum of the red blood cell rouleau. Collection of Membrane Society of Japan No. 2. Lecture subject matter. Apr. 30, 2007, p. 31.
Asami et al., Dielectric behavior of non-spherical cells in culture. Biochimica et Biophysica Acta. 1995, vol. 1245, pp. 317-324.

* cited by examiner

*Primary Examiner* — Pablo S Whaley
(74) *Attorney, Agent, or Firm* — Wolf, Greenfield & Sacks, P.C.

(57) ABSTRACT

The present invention relates to a method for measuring physical property values of a cell based on dielectric spectroscopy and based on modeling electrical characteristics such as electric conductivity, electric permittivity, dielectric constant change, and dielectric relaxation expressions in order to obtain membrane capacitance and cytoplasmic conductivity values of the cell.

7 Claims, 6 Drawing Sheets

METHOD FOR MEASURING PHYSICAL PROPERTY VALUES OF A CELL

TECHNICAL FIELD

The present invention relates to a method and an apparatus for measuring physical property values of a cell. More specifically, the invention relates to a technique for measuring electrical characteristics of a cell by utilizing a dielectric spectroscopy.

BACKGROUND ART

In general, it is known that in a cell, physical property values exhibiting electrical characteristics such as an electric conductivity, an electric permittivity, and a dielectric constant change depending on kinds, statuses or the like of the cell. For example, a muscle cell and a nerve cell show high values of electric conductivities (hereinafter referred to as a cell cytoplasm conductivities) of an extracellular fluid and an intracellular fluid as compared with the case of a skin cell containing therein less water. In addition, when the electric permittivity of the cell is measured by sweeping a frequency, dielectric relaxation characteristics change depending on forms of the cell. Thus, by utilizing such characteristics, qualitative and quantitative analyses, and identification of the cell, and moreover confirmation of presence or absence of a disease, and the like become possible. Also, heretofore, a technique for utilizing a difference in dielectric characteristics between the cells has also been proposed as an identification method in separating the cells or the like from each other by a flow cytometry (for example, refer to Parent Documents 1 and 2).

On the other hand, since the cell causes interfere polarization (Maxwell-Wagner polarization) under an electric field, when a dielectric spectroscopy measurement is carried out with respect to a solution containing therein cells, a frequency dispersion of a complex electric permittivity is obtained. Also, when a relaxation expression such as a Maxwell-Wagner equation is applied to the resulting dielectric spectrum, physical property values exhibiting the electrical characteristics of the cell, such as a cell cytoplasm electric conductivity $\kappa_i$ and a membrane capacitance $C_m$ are obtained. The electrical characteristics of the cell such as a blood cell are measured by utilizing the dielectric spectroscopy in such a manner, thereby making it possible to know the state of the cell in a nondisruptive manner.

Patent Document 1: Publication of the Translation of JP-T-2003-507739
Patent Document 2: Publication of the Translation of JP-T-2005-512042

DISCLOSURE OF INVENTION

Figure 10:
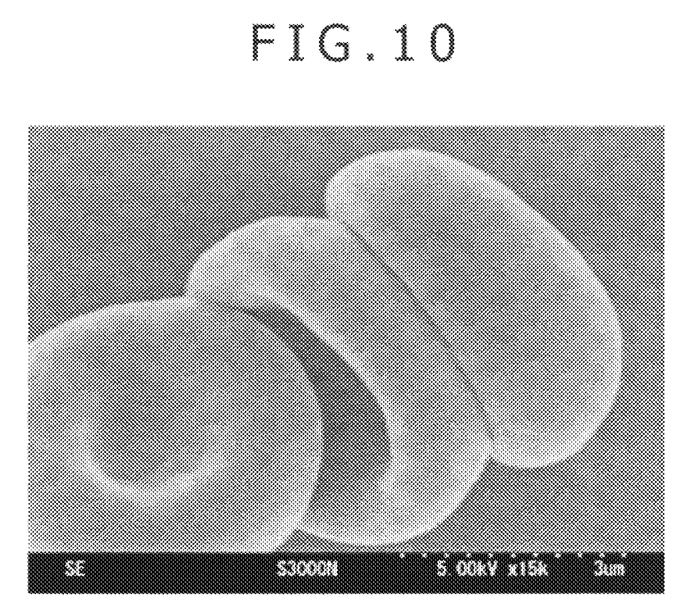
FIG. 10 is a picture (SEM picture at 15000-fold magnification) used as a substitute for a drawing showing the Discocytes.
Figure 11:
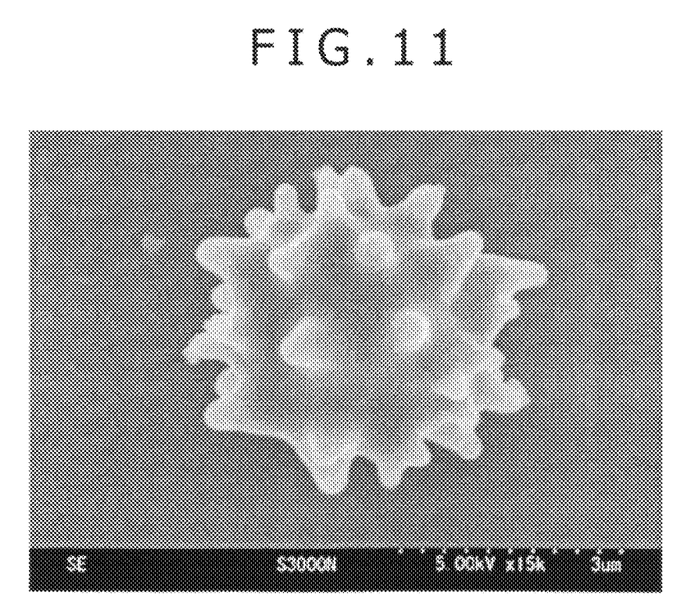
FIG. 11 is a picture (SEM picture at 15000-fold magnification) used as a substitute for a drawing showing the Echinocyte.

However, the prior art described above involves the problems shown below. That is to say, there is encountered such a problem that although the interface polarization is largely influenced by the shape of the cell, the Maxwell-Wagner equation which has been conventionally used in the analysis is established only in the cell having either a spherical shape or an ellipsoidal shape. FIG. 10 is a Scanning Electron Microscope (SEM: 1500-fold magnification) picture showing Discocytes, and FIG. 11 is a SEM picture (1500-fold magnification) showing an Echinocyte. As shown in FIG. 10, a red blood cell having a normal shape is of a disc-like shape having a dimple at the center thereof. In addition, since the shape of the blood cell sensitively changes depending on a state of the body, a disease or the like, there is also the red blood cell having the echin-shape as shown in FIG. 11. Although as has been described, the cells having the various kinds of shapes exist, the method utilizing the dielectric spectroscopy can not be applied to any of the cells having the respective shapes other than the spherical shape and the ellipsoidal shape. Thus, heretofore, with regard to these cells having the nonisotropic shapes, the physical property values exhibiting the electrical characteristics such as the cell cytoplasm electric conductivity $\kappa_i$ and the membrane capacitance $C_m$ have been unable to be known in the nondisruptive manner.

In the light of the foregoing, it is therefore a principal object of the present invention to provide a method of measuring physical values of a cell, and a physical property measuring apparatus with each of which with respect to a cell as well having a nonisotropic shape, physical property values exhibiting electrical characteristics thereof can be measured in a nondisruptive manner.

A method of measuring physical property values of a cell according to the present invention has: a process for calculating a dielectric spectrum about a cell having a specific shape by setting an arbitrary membrane capacitance $C_m$ and an arbitrary cell cytoplasm electric conductivity $\kappa_i$, thereby carrying out a numeral analysis; a process for obtaining a rise $\Delta\in$ in relative electric permittivity and relaxation time $\tau$ of the cell by revolving the dielectric spectrum to a dielectric relaxation expression; and a process for creating a regression expression corresponding to a shape of the cell based on the rise $\Delta\in$ in relative electric permittivity and the relaxation time $\tau$.

The method of measuring physical property values of a cell, in addition to the processes described above, may further have a process for measuring the dielectric spectrum of the cell, and comparing the measurement result and the regression expression with each other, thereby obtaining a membrane capacitance $C_{m,\,exp}$ and a cell cytoplasm electric conductivity $\kappa_{i,\,exp}$ of the cell.

In addition, it is also possible that the regression expression is created every shape of the cell, and a membrane capacitance $C_{m,\,exp}$ and a cell cytoplasm conductivity $\kappa_{i,\,exp}$ are obtained by application of the regression expression corresponding to the shape of the cell.

Moreover, the cell, for example, may also have a nonisotropic shape.

On the other hand, a physical property measuring apparatus according to the present invention has: means for calculating a dielectric spectrum about a cell having a specific shape by setting an arbitrary membrane capacitance $C_m$ and an arbitrary cell cytoplasm electric conductivity $\kappa_i$, thereby carrying out a numeral analysis; means for obtaining a rise $\Delta\in$ in relative electric permittivity and relaxation time $\tau$ of the cell by revolving the dielectric spectrum to a dielectric relaxation expression; and means for creating a regression expression corresponding to a shape of the cell based on the rise $\Delta\in$ in relative electric permittivity and the relaxation time $\tau$.

According to the present invention, the dielectric spectrum actually measured, and the regression expression created by the simulation are compared with each other, thereby determining the membrane capacitance $C_{m,\,exp}$ and the cell cytoplasm electric conductivity $\kappa_{i,\,exp}$ of the cell as an object of the measurement. Therefore, with respect to the cell as well, having the nonisotropic shape, which is not adapted to the conventional relaxation expression, the physical property values exhibiting the electrical characteristics such as the cell cytoplasm electric conductivity $\kappa_i$ and the membrane capacitance $C_m$ of that cell can be obtained in the nondisruptive manner.

BRIEF DESCRIPTION OF DRAWINGS

FIGS. 4(a) and (b) are respectively diagrams each showing a regression curved surface of the Discocyte obtained through a calculation.

FIGS. 5(a) and (b) are respectively diagrams each showing a regression curved surface of the Echinocyte obtained through a calculation.

BEST MODE FOR CARRYING OUT THE INVENTION

Figure 1:
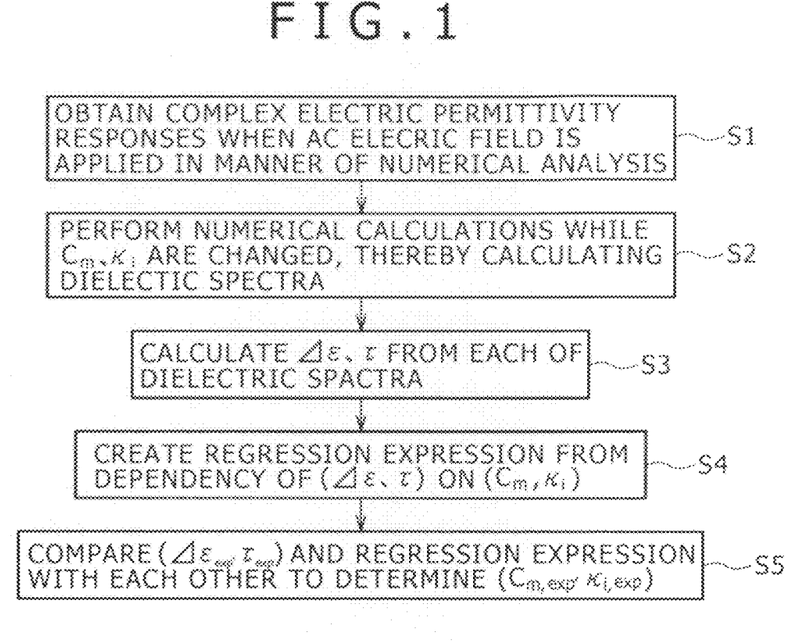
FIG. 1 is a flow chart showing a method of measuring physical property values of a cell according to an embodiment of the present invention in the order of processes thereof.

Hereinafter, Best Mode for Carrying Out the Invention will be described in detail with reference to the accompanying drawings. FIG. 1 is a flow chart showing a method of measuring physical property values of a cell according to an embodiment of the present invention in the order of processes thereof. As shown in FIG. 1, in the method of measuring physical property values of a cell of this embodiment (hereinafter simply referred to as a measurement method as well), firstly, with regard to cells, each having a nonisotropic shape, such as a normal red blood cell and Echinocyte, complex electric permittivity responses when an AC electric field is applied to specific isotropic three-dimensional shapes in each of which an outer phase and an inner phase are partitioned by a thin membrane are obtained in a manner of a numerical analysis by using models of shapes of the cells each having the nonisotropic shape (Step S1). Although a calculation method at this time is especially by no means limited, for example, a three-dimensional finite difference method or the like can be utilized.

Next, the numerical calculations are carried out based on the complex electric permittivity responses obtained in Step S1 while the membrane capacitance $C_m$ and the cell cytoplasm electric conductivity $\kappa_i$ are changed independently of each other, thereby calculating dielectric spectra of the cells having the respective shapes (Step S2).

Next, two parameters of a rise $\Delta \in$ in relative electric permittivity and relaxation time $\tau$ are calculated from each of the dielectric spectra obtained in Step S2 (Step S3). Although the dielectric spectrum of each of the cells can not be perfectly expressed by a simple relaxation expression, by revolving the dielectric spectrum of each of the cells to a Cole-Cole type relaxation expression shown in Expression 1 which will be shown below, the dielectric spectrum of each of the cells can be converted into three values exhibiting dielectric relaxation characteristics, that is, the rise $\Delta \in$ in relative electric permittivity, the relaxation time $\tau$, and a Cole-Cole parameter $\beta$ exhibiting the spreading of the relaxation. Then, in this embodiment, a real part ($\in'$) of each of the dielectric spectra obtained from the calculations is fitted by using the Cole-Cole type relaxation expression shown in Expression 1 which will be shown below, thereby obtaining the rise $\Delta \in$ in relative electric permittivity, and the relaxation time $\tau$. It is noted that in Expression 1 which will be shown below, $\omega$ is an angular frequency, $\in_0$ is an electric permittivity of a vacuum, $\kappa_1$ is an electric conductivity of a solution in a low frequency limit, $\in_-$ is a relative electric permittivity in a high frequency limit, and $i^2 = -1$.

$$\in^*(\omega) = \Delta\in/\{1+(i\times\omega\times\tau)^\beta\} + \in_- + \kappa_i/(i\times\omega\times\in_0) \quad [\text{Expression 1}]$$

Next, dependency of the rise $\Delta \in$ in relative electric permittivity, and the relaxation time $\tau$ on $(C_m, \kappa_i)$ is obtained every shape of the cell based on the rise $\Delta \in$ in relative electric permittivity, and the relaxation time $\tau$ calculated in Step S3, thereby creating a regression expression (Step S4). Although coefficients obtained from each of the dielectric spectra are largely influenced by the shape of the cell, it is thought that since the essence of the polarization of the cell is the interface polarization, the dependency of the rise $\Delta \in$ in relative electric permittivity, and the relaxation time $\tau$ on $(C_m, \kappa_i)$ form the same function form as that of the Maxwell-Wagner equation. Thus, in the measurement method of the present invention, a relationship shown in Expression 2 and Expression 3 which will be shown below was set, and a multiple regression analysis of constants a, b, c and d was carried out for the results obtained in Step S3, thereby obtaining the dependency of the rise $\Delta \in$ in relative electric permittivity, and the relaxation time $\tau$ on $(C_m, \kappa_i)$. It is noted that P in Expression 2 shown below is a volume fraction of the cell which is obtained from the model of each of the shapes used in Step S1.

$$\Delta\in/P = f(C_m, \kappa_i) = (a \times C_m)/(1 + b \times \kappa_i) \quad [\text{Expression 2}]$$

$$\tau = g(C_m, \kappa_i) = C_m \times (C/\kappa_i + d) \quad [\text{Expression 3}]$$

In such a manner, the frequency dispersion of the complex electric permittivity is obtained every shape of the cell in advance in the manner of the numerical analysis and the results of the numerical analysis are made to revolve to the dielectric relaxation expression, thereby creating the regression with respect to the dependency of the rise $\Delta \in$ in relative electric permittivity, and the relaxation time $\tau$ on $(C_m, N_i)$. Therefore, with regard to the cell as well, having the nonisotropic shape, which is not adapted to the conventional relaxation expression, the physical property values exhibiting the electrical characteristics such as the cell cytoplasm electric conductivity $\kappa_i$ and membrane capacitance $C_m$ thereof can be speedily and easily measured in the nondisruptive manner.

In addition, when the cell cytoplasm electric conductivity $\kappa_i$ and the membrane capacitance $C_m$ of the cell are obtained by using the measurement method of this embodiment, firstly, with respect to the cell as the object of the measurement which is dispersed into a normal saline solution or the like, a complex electric permittivity thereof is measured by sweeping a frequency by using an impedance analyzer or the like. Next, a real part ($\in'$) of the resulting dielectric spectrum is fitted by using the Cole-Cole type relaxation expression shown in Expression 1 described above, thereby obtaining a rise $\Delta\in_{exp}$ in relative electric permittivity, and relaxation time $\tau_{exp}$. Also, ($\Delta\in_{exp}$, $\tau_{exp}$) and a regression expression (f($C_m$, $\kappa_i$), g($C_m$, $\kappa_i$)) created in Step S4 are compared with each other, thereby determining a membrane capacitance $C_{m,\ exp}$ and the cell cytoplasm electric conductivity $\kappa_{i,\ exp}$ of the cell as the object of the measurement (Step S5).

As has been described, in the measurement method of this embodiment, the dielectric spectrum actually measured and the regression expression created by the simulation are compared with each other, thereby determining the membrane capacitance $C_{m,\ exp}$ and the cell cytoplasm electric conductivity $\kappa_{i,\ exp}$ of the cell as the object of the measurement. Therefore, with regard to the cell as well, having the nonisotropic shape, which is not adapted to the conventional relaxation expression, the physical property values exhibiting the electrical characteristics thereof can be measured in the nondisruptive manner. In addition, of the dielectric spectra which are obtained by estimating unknown amounts about the cell cytoplasm electric conductivity and the like, thereby carrying out numerous calculations, the dielectric spectrum which most coincides with the dielectric spectrum actually measured, whereby the labor and time required for the measurement can be greatly shortened as compared with the conventional method of deriving the suppression number of measurement specimens.

In addition, the physical property values of the cell which are determined by using the measurement method of this embodiment can be converted into information such as desorption of a membrane protein and abnormality of a cell cytoplasm to be used in diagnosis of a disease or the like. Moreover, for example, in a blood cell counter, not only the counting, but also up to the state of the blood cell can be simultaneously measured at a high speed, and also a statistical study about a rate of abnormal cells, and the like becomes possible.

It should be noted that in the embodiment described above, the case where the cell cytoplasm electric conductivity $\kappa_i$ and the membrane capacitance $C_m$ are obtained has been described as an example, the present invention is by no means limited thereto. Thus, with regard to the physical property values of the cell, in addition to the cell cytoplasm electric conductivity $\kappa_i$ and the membrane capacitance $C_m$, for example, a membrane electric conductivity, a cell cytoplasm electric conductivity, and the like can also be measured.

In addition, the measurement method of this embodiment can be carried out by using an apparatus for carrying out the processes described above. All it takes for the apparatus for measuring physical property values of a cell used in this embodiment is to include at least means for calculating a dielectric spectrum about a cell having a specific shape by setting an arbitrary membrane capacitance $C_m$ and an arbitrary cell cytoplasm electric conductivity $\kappa_i$, thereby carrying out a numeral analysis; means for obtaining a rise $\Delta\in$ in relative electric permittivity and relaxation time $\tau$ of the cell by revolving the dielectric spectrum to a dielectric relaxation expression; and means for creating a regression expression corresponding to a shape of the cell based on the rise $\Delta\in$ in relative electric permittivity and the relaxation time $\tau$.

EXAMPLE

Hereinafter, an example of the present invention will be compared with a comparative example departing from the scope of the present invention to concretely describe the effects thereof. It should be noted that the present invention is by no means limited to the example which will be described below. In this example, cell cytoplasm electric conductivities $\kappa_i$ and the membrane capacitances $C_m$ of cells having various kinds of shapes were measured by using the method of measuring physical property values of a cell shown in FIG. 1.

Firstly, a rabbit preserved blood (made by KOHJINBIO Co., Ltd.) was subjected to centrifugal processing, thereby extracting only red blood cells. Also, the red blood cells thus extracted were dispersed into a normal saline solution a concentration of which was adjusted so as to have pH5.3, thereby preparing a specimen (No. 1) of the Spherocytes. The red blood cells thus extracted were dispersed into a normal saline solution a concentration of which was adjusted so as to have pH8.5, thereby preparing a specimen (No. 2) of the Discocytes. Also, the red blood cells thus extracted were dispersed into a normal saline solution a concentration of which was adjusted so as to have pH7.7, thereby preparing a specimen (No. 3) of the Echinocytes. It should be noted that although for the purpose of obtaining the Spherocytes, in general, the specimen was prepared by utilizing a difference in osmotic pressure, in this example, in order to unify the shapes of the blood cells, the specimens were prepared by using the technique described above. In addition, each of the specimens was observed by using a microscope, and as a result, a ratio of the red blood cells each having the shape as the object of the measurement to the total number of red blood cells was 90% or more in a fraction of a quantity. Moreover, in this example, for the purpose of reference, a specimen (No. 4) was also prepared by dispersing Normocytes into a phosphate buffered saline (PBS).

Next, with respect to each of the specimens prepared by using the method described above, the electric permittivity was measured while the electrode polarization was suppressed in the range of 10 kHz to 110 MHz by using an impedance analyzer (4294A made by Agilent Technologies, Inc.). Also, with respect to the specimen (No. 1) of the Spherocytes, known values, that is, a relative electric permittivity $\in_a = 78.3$, an electric conductivity $\kappa_a = 1.67$ S/m, and cell membrane electric conductivity $\kappa_m = 1 \times 10^{-7}$ S/m of an outer aqueous phase were used, and the Maxwell-Wagner equation for a thin shell was applied to a dielectric spectrum obtained through the measurement, thereby obtaining a volume fraction P, a membrane capacitance $C_m (= \in_m \cdot \in_0 / d_m$ where $d_m$ is a thickness of a membrane, $\tau_m$ is a relative electric permittivity of the membrane, and $\tau_0$ is an electric permittivity of the vacuum) per unit area of the cell membrane, and an electric permittivity $\in_i$ and an electric conductivity $\kappa_i$ of an inner aqueous phase of the red blood cell.

Figure 2:
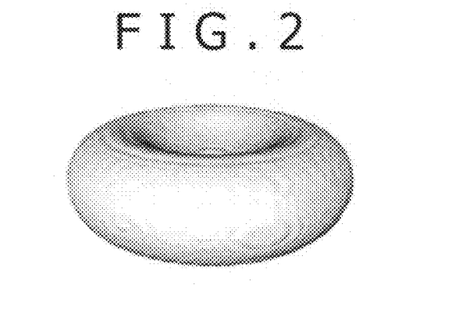
FIG. 2 is a view showing a simulation model of a Discocyte.
Figure 3:
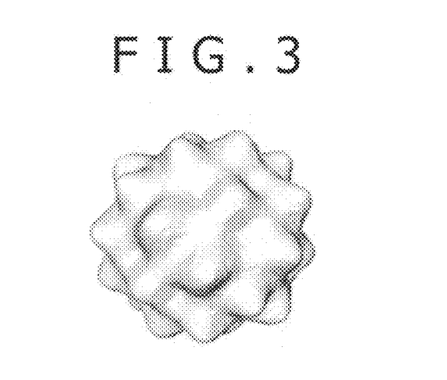
FIG. 3 is a view showing a simulation model of an Echinocyte.

On the other hand, with respect to the Discocytes and the Echinocytes, the volume fraction P was calculated by using an ellipsoidal model and a spherical model, and a complex electric permittivity was obtained through a simulation using a three-dimensional finite difference method. It is noted that a length of a long axis of a Discocyte was measured by using a light microscope, and as a result, it was proved to be about 7.9 μm which was approximately equal to that of the shape of the red blood cell (RBC) of the human. Then, a simulation of the Discocyte was carried out by reference to the expression of the RBC of the human. In addition, although the Echinocytes also have a variety in the numbers of protrusions, and thus the Echinocytes having various kinds of shapes exist, in this example, the simulation was carried out based on the result of the observation made by using the light microscope. FIG. 2 is a view showing a simulation model of the Discocyte, and FIG. 3 is a view showing a simulation model of the Echinocyte.

When the assumption of the diluteness is established, in the normal shape, the resolutions are obtained in the case where the direction of the principal axis and the electric field either intersect perpendicularly with each other or are parallel with each other, and they are weighted with the probability density to be averaged, thereby making it possible to obtain the complex electric permittivity. Then, the calculation was carried out with a small volume fraction P (P≦0.04%) so that the assumption of the diluteness is established, and the calculation results ($\in'$, $\in''$) were normalized by P as shown in Expression 4 and Expression 5 which will be shown below. It is noted that $\kappa_l$ in Expression 5 shown below is an electric conductivity in a low frequency limit.

$$\in' = (\in - \in_a)/P \quad \text{[Expression 4]}$$

$$\in'' = (\kappa - \kappa_l)/(\in_v \times \omega \times P)$$

Figure 4:
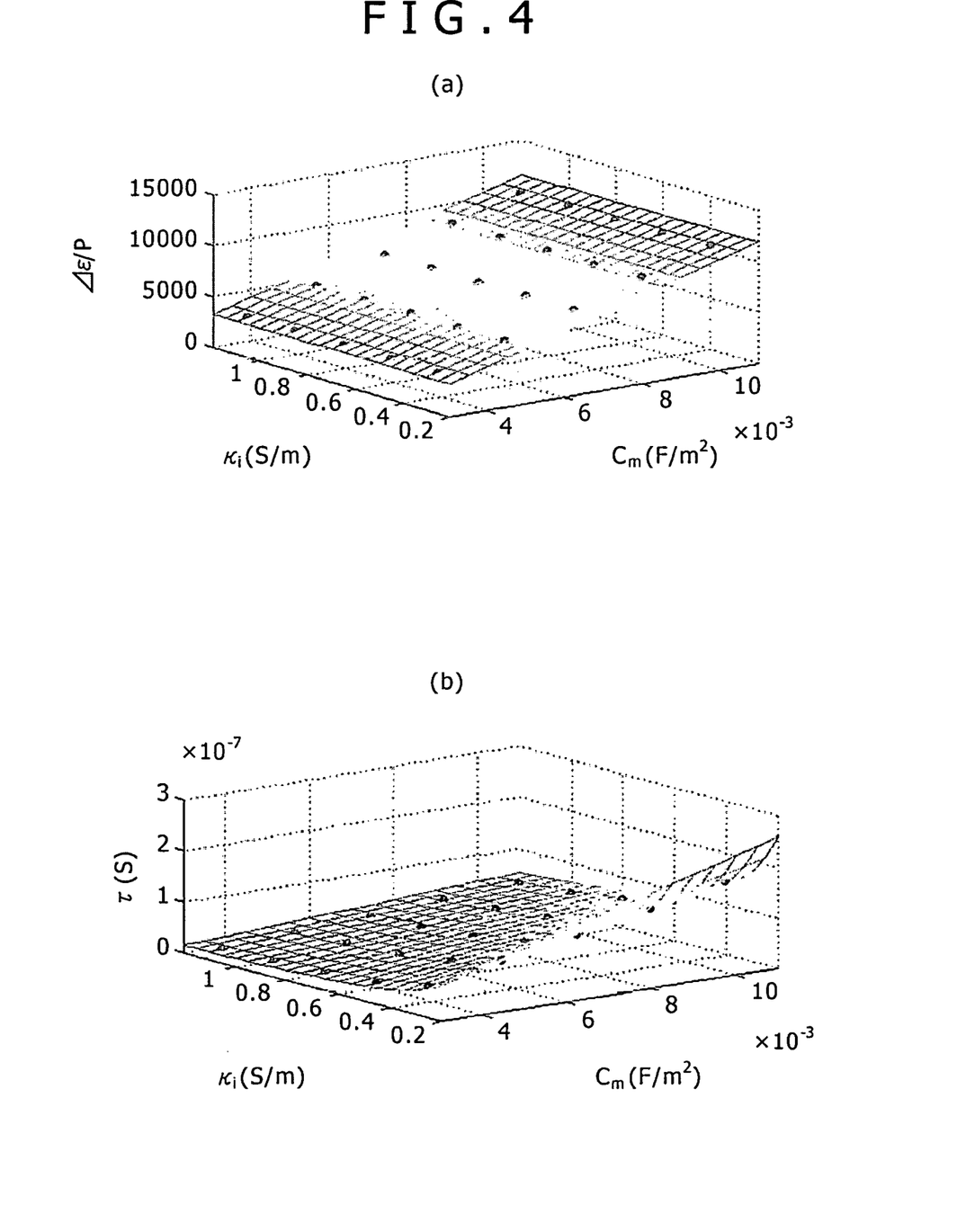
FIG. 4(a) is a 3D curved surface about a rise $\Delta \in$ in relative electric permittivity and FIG. 4(b) is a 3D curved surface about relaxation time $\tau$.
Figure 5:
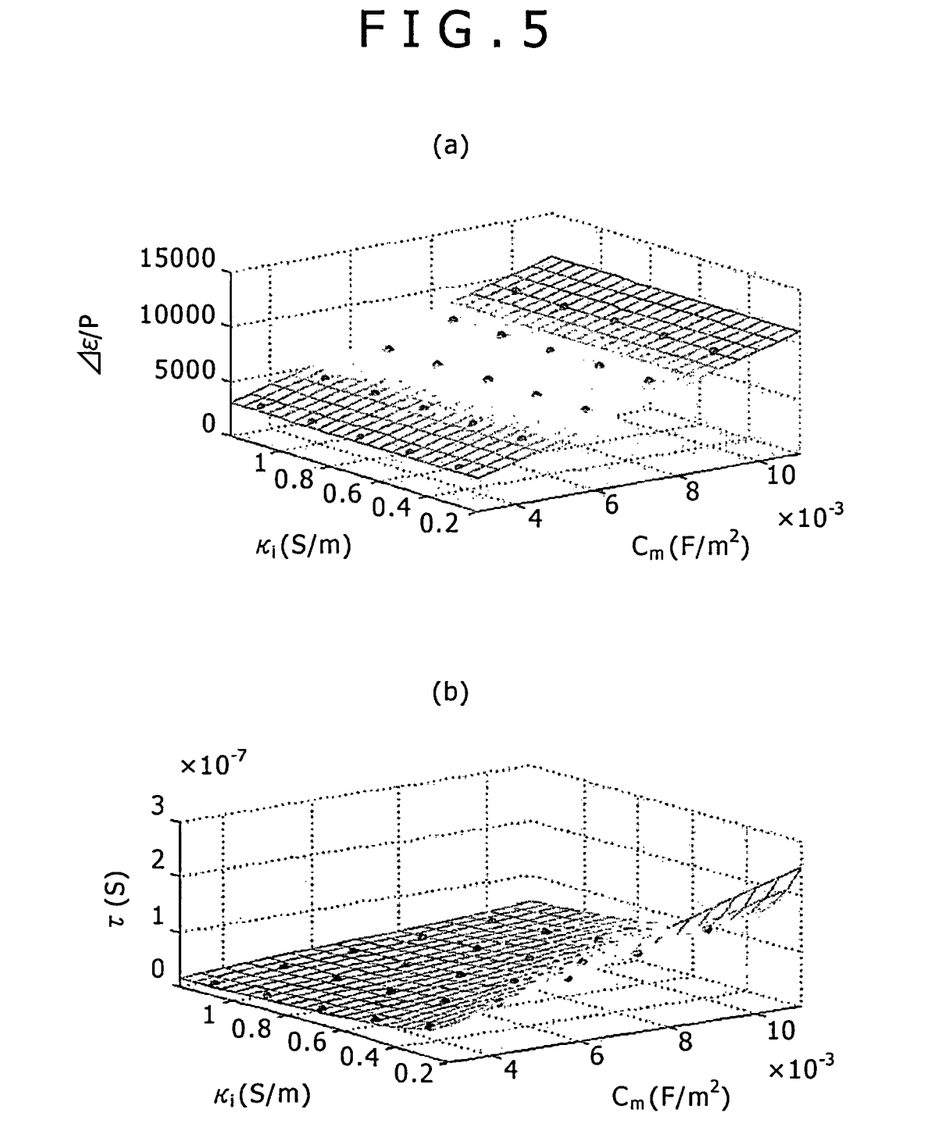
FIG. 5(a) is a 3D curved surface about a rise $\Delta \in$ in relative electric permittivity and FIG. 5(b) is a 3D curved surface about relaxation time $\tau$.

Next, the numerical calculation about the shapes were carried out under the 25 conditions in total with respect to the Discocyte and the Echinocyte while the membrane capacitance $C_m$ and the cell cytoplasm electric conductivity $\kappa_i$ were changed independently of each other, thereby calculating the dielectric spectra with respect to the Discocyte and the Echinocyte, respectively. After that, for the purpose of easily characterizing the dielectric spectra obtained through the calculations, the respective time particles were fitted by using the Cole-Cole type relaxation expression shown in Expression 1, thereby calculating the rise Δ$\in$ in relative electric permittivity and the relaxation time τ. Also, the multiple regression analysis was carried out for the calculation results about the 25 conditions, thereby determining the constants a, b and c in Expression 2 and Expression 3 described above. As a result, in the case of the Discocyte, the values of a=1.10×10$^6$ m$^2$/F, b=2.86×10$^{-2}$ m/S, c=4.52×10$^{-6}$ m, and d=1.19×10$^{-6}$ m$^2$/S were obtained. In addition, in the case of the Echinocyte, the values of a=2.08×10$^6$ m$^2$/F, b=5.26×10$^{-3}$ m/S, c=1.02×10$^{-5}$ m, and d=2.16×10$^{-6}$ m$^2$/S were obtained. FIGS. 4(*a*) and (*b*) are respectively diagrams showing regression curved surfaces of the Discocyte. FIG. 4(*a*) is a 3D curved surface about the rise Δ$\in$ in relative electric permittivity, and FIG. 4(*b*) is a 3D curved surface about the relaxation time τ. In addition, FIGS. 5(*a*) and (*b*) are respectively diagrams showing regression curved surfaces of the Echinocyte. FIG. 5(*a*) is a 3D curved surface about the rise Δ$\in$ in relative electric permittivity, and FIG. 5(*b*) is a 3D curved surface about the relaxation time τ.

Figure 6:
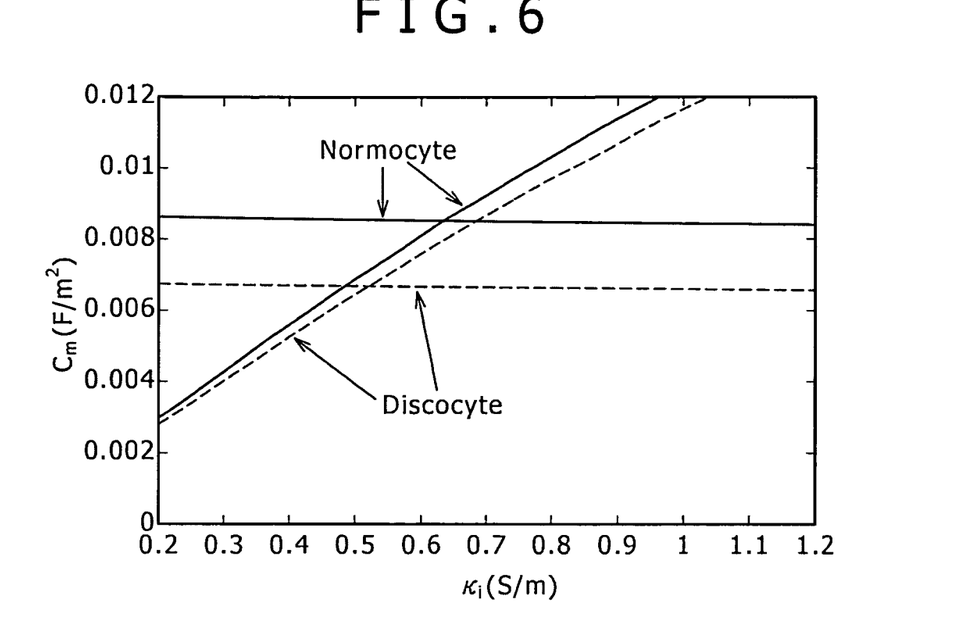
FIG. 6 is a graph showing a relationship between values obtained through a calculation and values actually measured with respect to the Discocyte with a cell cytoplasm electric conductivity $\kappa_i$ being platted on an axis of abscissa and a membrane capacitance $C_m$ being plotted on an axis of ordinate.
Figure 7:
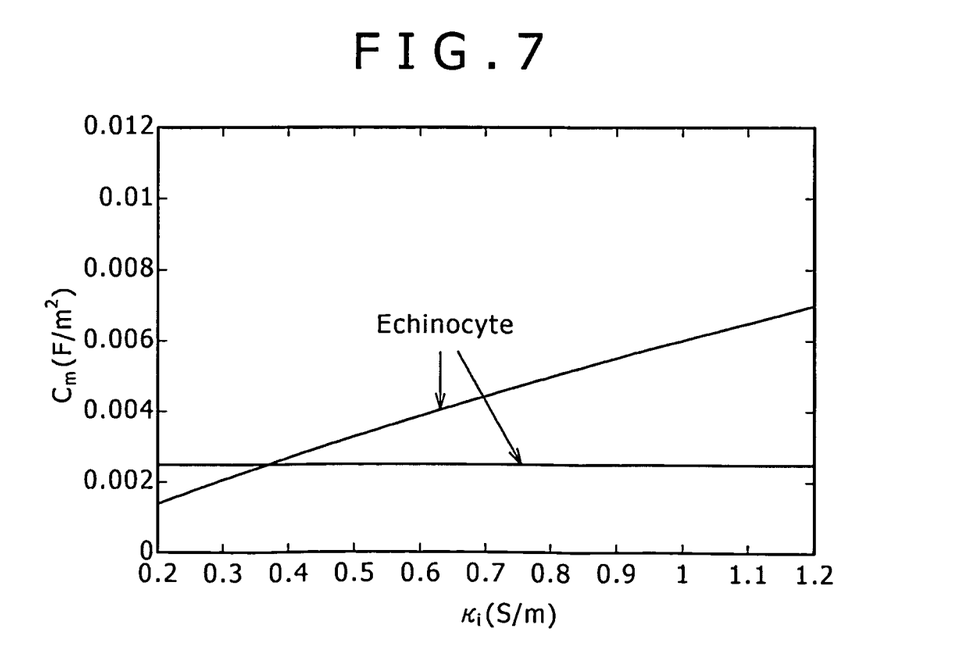
FIG. 7 is a graph showing a relationship between values obtained through a calculation and values actually measured with respect to the Echinocyte with a cell cytoplasm electric conductivity $\kappa_i$ being platted on an axis of abscissa and a membrane capacitance $C_m$ being plotted on an axis of ordinate.

Next, with regard to the dielectric spectra (values actually measured) of the specimens of No. 2 and No. 3 in each of which the cell cytoplasm electric conductivity $\kappa_i$ and the membrane capacitance $C_m$ were unknown, similarly, the real part ($\in'$) of the complex electric permittivity thereof was fitted by using the Cole-Cole type relaxation expression shown in Expression 1 described above, thereby calculating the relaxation parameters (Δ$\in_{exp}$, $\tau_{exp}$). Also, curved surfaces which the regression curved surfaces shown in FIG. 4 and FIG. 5, and Δ$\in$=Δ$\in_{exp}$ and τ=$\tau_{exp}$ have in common were respectively obtained. FIG. 6 is a graphical representation showing a relationship between values obtained through calculations about the Discocyte, and values actually measured with the cell cytoplasm electric conductivity $\kappa_i$ being plotted on an axis of abscissa and the membrane capacitance $C_m$ being platted on an axis of ordinate, and FIG. 7 is a graphical representation showing a relationship between values obtained through calculations about the Echinocyte, and values actually measured with the cell cytoplasm electric conductivity $\kappa_i$ being plotted on an axis of abscissa and the membrane capacitance $C_m$ being platted on an axis of ordinate. It is noted that FIG. 6 shows the relationship in the case of the Discocyte together with values as well of the Normocyte. Also, the membrane capacitance $C_{m,\,exp}$ and the cell cytoplasm electric conductivity $\kappa_{i,\,exp}$ of each of the measurement specimens (No. 2 and No. 3) were determined from an intersection point between each two curve lines shown in FIG. 6 and FIG. 7. The values of the membrane capacitances $C_{m,\,exp}$ and the cell cytoplasm electric conductivities $\kappa_{i,\,exp}$ of the specimens of No. 1 to No. 4 which have been determined from the processes described above are collectively shown in Table 1.

TABLE 1

| Specimen | | Volume | Membrane | Cell cytoplasm electric |
|---|---|---|---|---|
| No. | Kind of cell | fraction P (%) | capacitance $C_m$ (F/m$^2$) | conductivity $K_i$ (S/m) |
| 1 | Spherocyte | 5.80 | 6.33 × 10$^{-3}$ | 0.713 |
| 2 | Discocyte | 7.18 | 6.68 × 10$^{-3}$ | 0.539 |
| 3 | Echinocyte | 8.73 | 2.54 × 10$^{-3}$ | 0.373 |
| 4 | Normocyte | 9.80 | 8.79 × 10$^{-3}$ | 0.666 |

Figure 8:
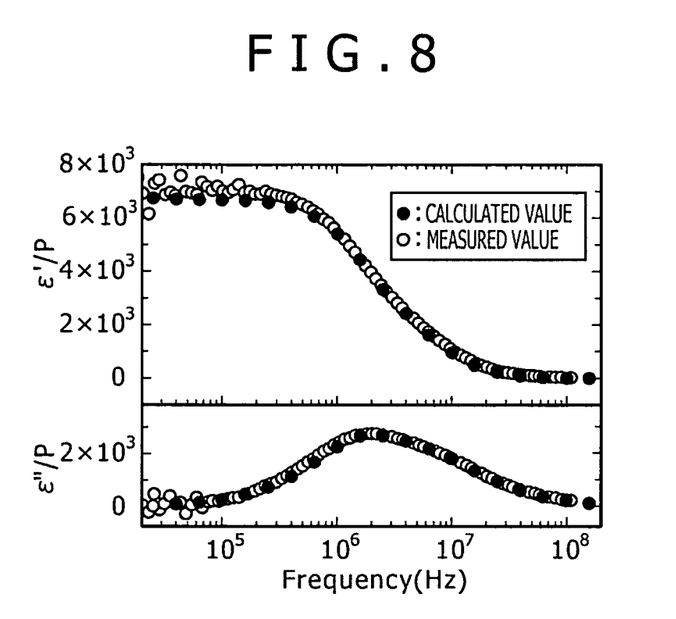
FIG. 8 is a graphical representation showing a dielectric dispersion of the Discocyte with a frequency being plotted on an axis of abscissa and a complex electric permittivity ($\in'$, $\in''$) being plotted on an axis of ordinate.
Figure 9:
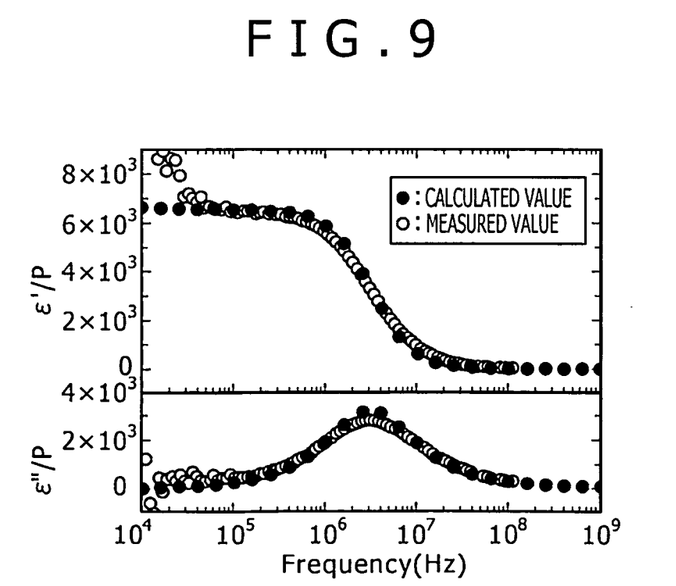
FIG. 9 is a graphical representation showing a dielectric dispersion of the Echinocyte with a frequency being plotted on an axis of abscissa and a complex electric permittivity ($\in'$, $\in''$) being plotted on an axis of ordinate.

In addition, for the purpose of confirming whether or not the values thus determined reproduced the dielectric dispersions actually measured, the dielectric dispersions of the Discocyte and the Echinocyte were calculated again by the finite difference method using the values obtained from FIG. 6 and FIG. 7. FIG. 8 is a graphical representation showing the dielectric dispersion of the Discocyte with the frequency being plotted on an axis of abscissa and the complex electric permittivity ($\in'$, $\in''$) being plotted on an axis of ordinate, and FIG. 9 is a graphical representation showing the dielectric dispersion of the Echinocyte with the frequency being plotted on an axis of, abscissa and the complex electric permittivity ($\in'$, $\in''$) being plotted on an axis of ordinate. As shown in FIG. 8 and FIG. 9, in any of the Discocyte and the Echinocyte, the calculation results reproduced the values actually measured. In particular, although the values actually measured exhibited the "awkward" spectrum unable to be expressed by the Cole-Cole expression which is generally applied to such a case, the calculation result about the Discocyte properly reproduced the values actually measured. From this, it was confirmed that the simple estimation processes described above for the phase constants were valid.

The invention claimed is:

1. A method of measuring physical property values of a cell having an isotropic or nonisotropic shape, the method comprising:
    applying an electric field to said cell at a frequency range within 10 kHz and 110 MHz;
    measuring an electric permittivity response from said cell based on the frequency range of the applied electric field, the measured electric permittivity response having a real part $\in'$ and an imaginary part $\in''$;
    determining a dielectric spectrum having a real part $\in'$ and an imaginary part $\in''$ about the cell based on the measured electric permittivity response and the isotropic or nonisotropic shape of the cell, wherein the dielectric spectrum is calculated by, at least in part, setting an arbitrary membrane capacitance $C_m$ and an arbitrary cell cytoplasm electric conductivity $\kappa_i$, and carrying out a numerical analysis according to the shape of the cell by independently changing the membrane capacitance $C_m$ and the cell cytoplasm electric conductivity $\kappa_i$ and matching the real part $\in''$ and the imaginary part $\in''$ of the dielectric spectrum to the real part $\in'$ and the imaginary part $\in''$ of the measured electric permittivity response;

determining a change $\Delta\in$ in relative electric permittivity and relaxation time $\tau$ of said cell depending on the membrane capacitance $C_m$ and the cell cytoplasm electric conductivity $\kappa_i$ by fitting the real part $\in''$ of the dielectric spectrum determined from the real part $\in'$ of the measured electric permittivity response to a dielectric relaxation expression comprising a Cole-Cole type relaxation expression, provided as follows:

$$\in^*(\omega)=\Delta\in/\{1+(i\times\omega\times\tau)^\beta\}+\in_-+\kappa_i/(i\times\omega\times\in_0)$$

including a Cole-Cole parameter $\beta$, an angular frequency $\omega$, an electric permittivity of a vacuum $\in_0$, an electric conductivity in a low frequency limit $\kappa_1$ and a relative electric permittivity in a high frequency limit $\in_-$;

forming a plurality of regression-expressions, provided as follows:

$$\Delta\in/P=f(C_m,\kappa_i)=(a\times C_m)/(1+b\times\kappa_i)$$

$$\tau=g(C_m,\kappa_i)=C_m\times(C/\kappa_i+d)$$

including constants a, b, c, d and a volume fraction of said cell P obtained from a model of the isotropic or nonisotropic shape of the cell, wherein the plurality of regression expressions correspond to the shape and dimensions of said cell based on the change $\Delta\in$ in relative electric permittivity and the relaxation time $\tau$;

performing a multiple regression analysis according to the plurality of regression expressions and determining the constants a, b, c and d; and determining an experimental membrane capacitance $C_{m,\,exp}$ and an experimental cell cytoplasm electric conductivity $\kappa_{i,\,exp}$ of said cell by comparing the measured electric permittivity response and the plurality of regression expressions with each other.

2. The method of claim 1, wherein the a plurality of regression expressions are formed for a plurality of cell shapes, and the experimental membrane capacitance $C_{m,\,exp}$ and the experimental cell cytoplasm electric conductivity $\kappa_{i,\,exp}$ are obtained by application of the plurality of regression expressions corresponding to each shape of said cell.

3. The method of claim 1, wherein:
said cell has a nonisotropic shape.

4. The method of claim 1, wherein applying the electric field comprises applying an AC electric field to said cell.

5. The method of claim 3, wherein said cell is at least one of a spherocyte, discocyte, or echinocyte.

6. The method of claim 1, wherein applying the electric field to said cell and measuring the electric permittivity response from said cell comprises use of an impedance analyzer.

7. The method of claim 1, wherein a complex electric permittivity is estimated through simulation using a three-dimensional finite difference method.

* * * * *